US00PP23725P3

(12) United States Plant Patent
Sills et al.

(10) Patent No.: US PP23,725 P3
(45) Date of Patent: Jul. 9, 2013

(54) BLACKBERRY PLANT NAMED 'DRISBLACKTHREE'

(50) Latin Name: ***Rubus* L. subgenus *Rubus***
Varietal Denomination: DrisBlackThree

(75) Inventors: Gavin R. Sills, Gilroy, CA (US); Andrea M. Pabon, Gilroy, CA (US); Carlos D. Fear, West Malling (GB)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 24 days.

(21) Appl. No.: 13/373,126

(22) Filed: Nov. 4, 2011

(65) Prior Publication Data

US 2013/0117896 P1 May 9, 2013

(51) Int. Cl.
*A01H 5/00* (2006.01)

(52) U.S. Cl.
USPC ..... Plt./203

(58) Field of Classification Search
USPC ..... Plt./203
See application file for complete search history.

*Primary Examiner* — Susan McCormick Ewoldt
(74) *Attorney, Agent, or Firm* — Jondle Plant Sciences Division of Swanson & Bratschun, L.L.C.

(57) ABSTRACT

This invention relates to a new and distinct variety of Blackberry plant named 'DrisBlackThree', which is primarily characterized by medium-sized, oblong fruit that matures to a black color, and having an early time of bud burst, is disclosed.

2 Drawing Sheets

Genus and species: *Rubus* L. subgenus *Rubus*.
Variety denomination: 'DrisBlackThree'.

BACKGROUND OF THE NEW PLANT

The present invention relates to a new and distinct Blackberry cultivar designated 'DrisBlackThree' and botanically known as *Rubus* L. subgenus *Rubus*. This new Blackberry variety was identified in Santa Cruz County, Calif. in July 2003 and originated from a cross between the female parent Blackberry plant 'Driscoll Carmel' (U.S. Plant Pat. No. 15,058) and the male parent Blackberry plant 'Zorro' (U.S. Plant Pat. No. 13,759). The original seedling of the new cultivar was first asexually propagated at a nursery in Santa Cruz County, Calif. in 2003. 'DrisBlackThree' was subsequently asexually propagated and underwent further testing at a nursery in Santa Cruz County, Calif. from 2003 to 2011. The present invention has been found to be stable and reproduce true to type through successive asexual propagations via tissue culture.

Plant Breeder's Rights for this variety have not been applied for. 'DrisBlackThree' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz, Calif.

1. Early bud burst; and
2. Oblong, medium-sized fruit.

DESCRIPTION OF THE PHOTOGRAPHS

This new Blackberry plant is illustrated by the accompanying photographs, which show the fruit of the plant as well as the cane. The colors shown are as true as can be reasonably obtained by conventional photographic procedures. The photographs are of plants that are 2 years old.

Figure 1:
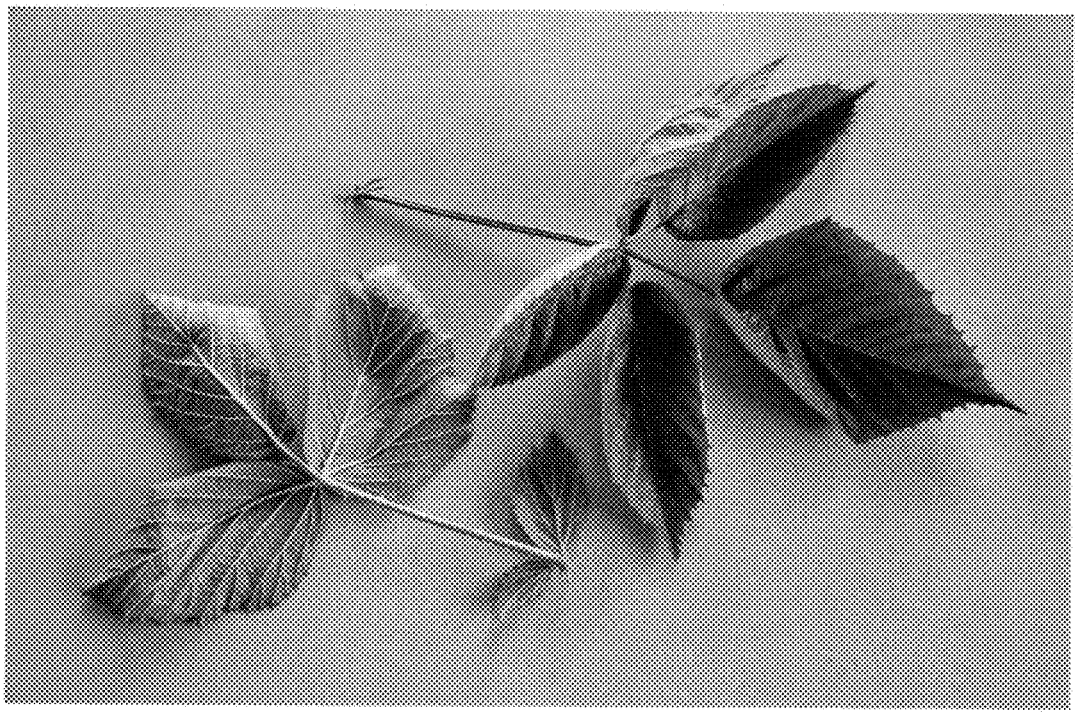
Figure 2:
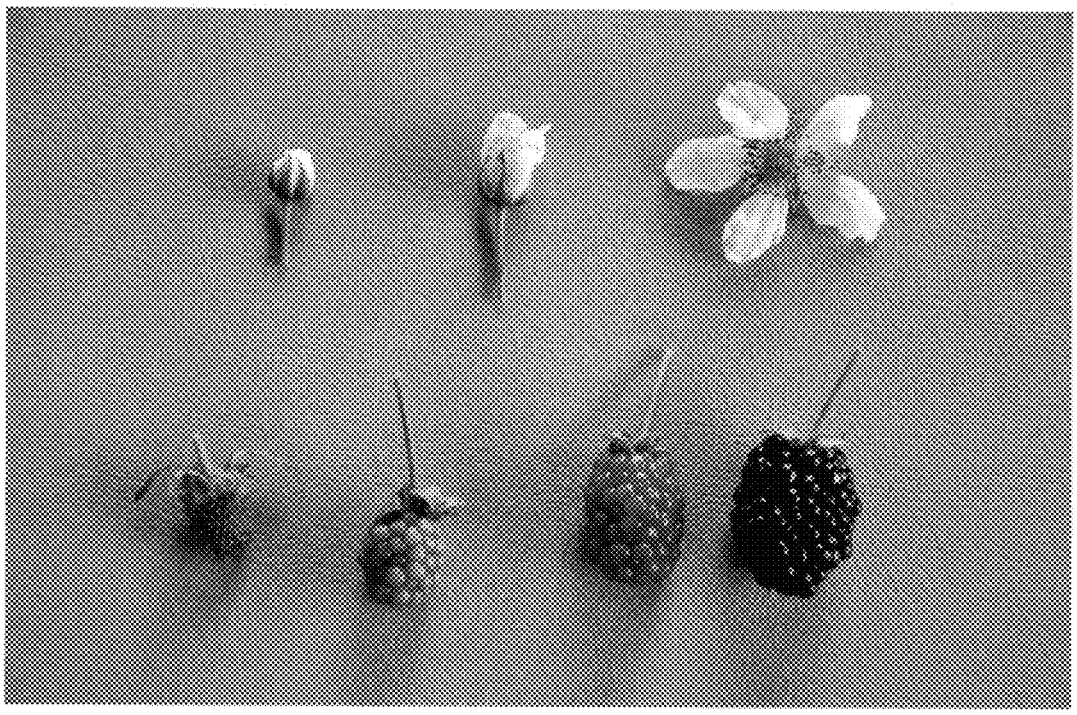
Figure 3:
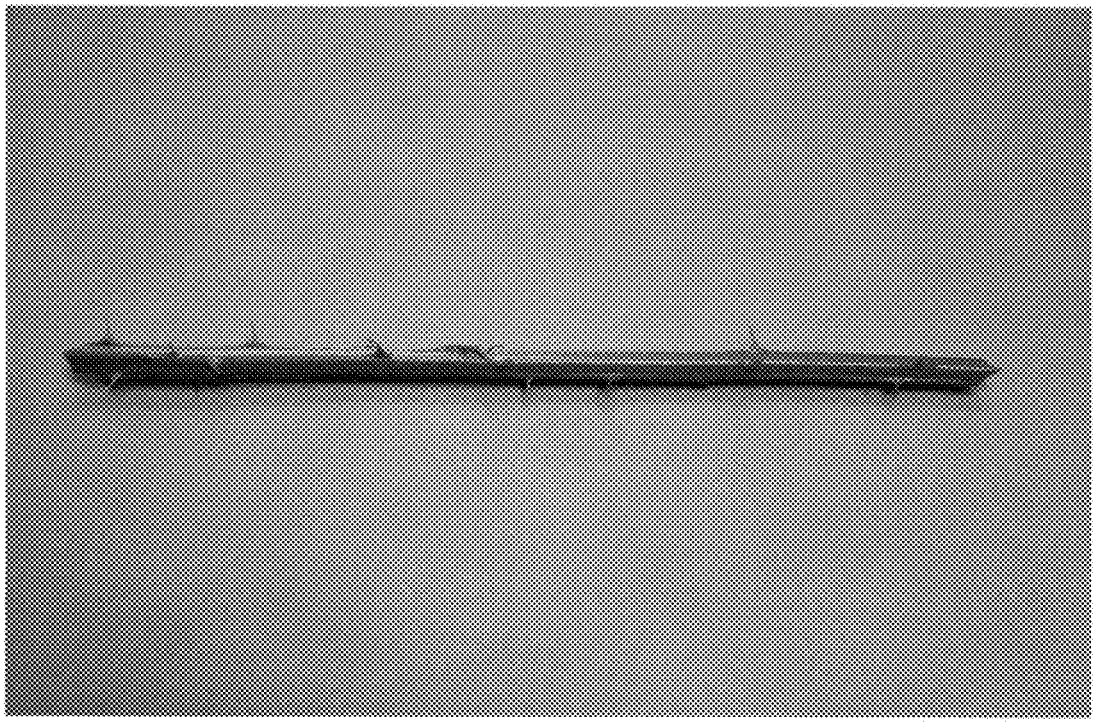

FIG. 1 shows the upper and lower side of the leaves.
FIG. 2 shows the flowers, and the fruit at various stages.
FIG. 3 shows a section of a young cane.

DESCRIPTION OF THE NEW VARIETY

The following description of 'DrisBlackThree' is based on observations of plants that were 2 years old in Santa Cruz County, Calif. This description is in accordance with UPOV terminology. Color designations, color descriptions, and other phenotypical descriptions may deviate from the stated values and descriptions depending upon variation in environmental, seasonal, climatic and cultural conditions. 'DrisBlackThree' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* $2^{nd}$ edition, by James G. Harris and Melinda Woolf Harris, unless where otherwise defined.

DETAILED BOTANICAL DESCRIPTION

Classification:
- *Family*.—Rosaceae.
- *Botanical*.—*Rubus* L. subgenus *Rubus*.
- *Common name*.—Blackberry.
- *Variety name*.—'DrisBlackThree'.

Parentage:
- *Female parent*.—Proprietary blackberry plant 'Driscoll Carmel' (U.S. Plant Pat. No. 15,058).
- *Male parent*.—Proprietary blackberry plant 'Zorro' (U.S. Plant Pat. No. 13,759).

Plant:
- *Vigor (health and hardiness of plant)*.—Medium.
- *Growth habit*.—Upright to semi-upright.

*Productivity*.—Medium.
*Propagation*.—Tissue culture and root cuttings.
*Self-fruitfulness*.—Self-fruitful.
*Time of bud burst*.—Early.

Canes:
*Fruiting lateral length* (*4th lateral from tip*).—Average: Medium; 7.2 cm. Range: 3.5 cm to 10.6 cm.
*Number of fruit per lateral*.—Average: 6.2. Range: 4 to 9.
*Fruiting on current year's cane*.—Absent.
*Cane internode length at central ⅓ of cane*.—Average: 3.5 cm. Range: 1.7 cm to 7.4 cm.
*Number of new canes during flowering*.—Medium.
*New cane strength* (*observed full-grown shoot after picking*).—Medium.
*Glaucosity observed on full-grown shoot after picking*.—Weak.
*Spines*.—Size: Medium. Color: RHS N144D (Medium yellow-green). Density on central third of cane: Medium. Texture: Coarse to rough. Attitude of apex in relation to cane: Downwards.
*Young shoots*.—Emergence from soil: Early. Anthocyanin coloration (during rapid growth): Medium; RHS 144A (Medium yellow-green). Intensity of green color: Medium. Number of glandular hairs: Absent or few.
*Dormant cane*.—Length: 8 feet. Diameter (in central third): 13.18 mm. Cross section (from mid cane observed at end of first growing season): Angular. Color: RHS 146B (Medium yellow-green). Number of branches: 8. Distribution of branches: Over whole length. Anthocyanin coloration: Medium; RHS 146B (Medium yellow-green). Spines: Present. Number of spines: 160.

Leaves:
*Type*.—Palmate.
*Predominant number of leaflets*.—3.
*Overlapping or relative position of lateral leaflets*.—Overlapping.
*Color*.—Upper surface: RHS 147A (Dark yellow-green). Lower surface: RHS 146A (Medium yellow-green).
*Arrangement*.—Compound (3 or more leaves per node).
*Glossiness*.—Weak.
*Cross section profile*.—Concave (margins rolled inwards).
*Time of leaf bud burst*.—January.
*Leaflets*.—Shape: Ovate. Margin: Doubly serrate. Depth of incisions: Medium. Apex: Truncate. Base: Obtuse. Rachis length between terminal leaflet and adjacent lateral leaflet: Average: 1.9 mm. Range: 1.1 mm to 2.4 mm.
*Lateral leaflet* (*basal pair*).—Length: Average: 8.4 mm. Range: 6.7 mm to 10.5 mm. Width: Average: 5.3 mm. Range: 4.1 mm to 7.4 mm. Length/width ratio: 1.6.
*Terminal leaflet*.—Length: Average: 9.8 mm. Range: 7.7 mm to 12.4 mm. Width: Average: 6.4 mm. Range: 5.3 mm to 8.6 mm. Length/width ratio: 1.5. Lobing: Absent. Undulation of margin (rippling of margin): Medium. Blistering between veins (rugosity): Medium. Shape: Ovate. Tip: Truncate. Base: Obtuse. Margin: Doubly serrate. Cross-section: U-shaped.
*Petiole*.—Length average: 6.4 mm. Length range: 4.3 mm to 9.5 mm. Width average: 1.5 mm. Width range: 1.2 mm to 1.8 mm. Pigmentation: Upper surface: Heavy; RHS 147A (Dark yellow-green). Lower surface: Medium; RHS 146A (Medium yellow-green).
*Stipule*.—Size: Medium. Orientation: Erect.

Inflorescence:
*Time of beginning of flowering on previous year's cane*.—April.
*Flower size*.—Medium.
*Flower diameter*.—Average: 4.33 mm. Range: 3.8 mm to 5.0 mm.
*Flower number* (*at 3rd node from tip of lateral*).—Average: 5. Range: 4 to 8.
*Petal*.—Length: Average: 2.34 mm. Range: 2.1 mm to 2.5 mm. Width: Average: 1.07 mm. Range: 1.0 mm to 1.20 mm. Color: RHS 155D (White).
*Pedicel*.—Length: Average: 3.69 mm. Range: 2.30 mm to 5.60 mm. Diameter: Average: 1.32 mm. Range: 1.10 mm to 1.70 mm.

Fruit:
*Time of ripening on previous year's cane*.—Early.
*Color*.—Immature: RHS 151A (Medium yellow-green). Maturing: RHS 183A (Dark greyed-purple). Mature: RHS 202A (Black).
*Glossiness*.—Medium.
*Shape in longitudinal section*.—Oblong.
*Size*.—Medium.
*Length*.—Average: 27.0 mm. Range: 23.0 mm to 33.0 mm.
*Width*.—Average: 19.9 mm. Range: 17.0 mm to 23.0 mm.
*Ratio of length to width*.—1.4; Medium.
*Weight* (*g/fruit*).—0.68.
*Soluble solids* (%) (*in Brix*).—11.2.
*Titratable acidity:* (% *as citric acid*).—1.1.
*Seed weight* (*g/seed*).—0.00287587.
*Number of druplets/fruit*.—110; Medium.
*Size of druplet*.—Medium.
*Firmness*.—Medium.
*Yield*.—Total yield: 91,351 lbs/acre. Marketable yield: 74,682 lbs/acre.

Disease, pest, and stress resistance:
*Botrytis fruit rot*.—Susceptible.
*Verticillium wilt*.—Susceptible.
*Leaf spots* (*Septoria rubi*).—Moderately susceptible.
*Tetranychus urticae*.—Susceptible.

COMPARISON WITH PARENTAL AND COMMERCIAL VARIETIES

'DrisBlackThree' differs from the female parent 'Driscoll Carmel' (U.S. Plant Pat. No. 15,058) in that 'DrisBlackThree' matures earlier, has smaller, firmer and less sweet fruit, and lower yield.

'DrisBlackThree' differs from the proprietary male parent 'Zorro' (U.S. Plant Pat. No. 13,759) in that the fruit of 'DrisBlackThree' is larger, more firm and sweeter than 'Zorro'.

'DrisBlackThree' differs from the commercial variety 'Driscoll Eureka' (U.S. Plant Pat. No. 14,765) in that 'DrisBlackThree' has an upright to semi-upright growth habit, early flowering, medium glossiness and oblong shaped fruit, while 'Driscoll Eureka' has an upright growth habit, very early flowering, strong glossiness and ovate shaped fruit.

We claim:

1. A new and distinct cultivar of Blackberry plant as described and shown herein.

* * * * *